United States Patent [19]

Noureldin et al.

[11] Patent Number: 5,551,421
[45] Date of Patent: Sep. 3, 1996

[54] DEVICE FOR SECUREMENT OF AN ENDOTRACHEAL TUBE IN A PATIENT'S MOUTH

[76] Inventors: Abdel H. Noureldin, 1315 Glenmore Ct., Barrington, Ill. 60010; Richard W. Carter, 935 Sandpiper Ct., Bartlett, Ill. 60103; Ahmed M. Noureldin, 133 Oliver Ct., Schaumburg, Ill. 60168

[21] Appl. No.: 335,594

[22] Filed: Nov. 8, 1994

Related U.S. Application Data

[63] Continuation of Ser. No. 861,465, Apr. 1, 1992, abandoned.

[51] Int. Cl.$^6$ .......................... A61M 16/00; A61M 5/32; A62B 9/06
[52] U.S. Cl. .......................... 128/207.17; 128/DIG. 26; 664/178; 664/179
[58] Field of Search .......................... 128/207.14–207.18, 128/207.29, 200.26, DIG. 15, DIG. 26; 664/174–180

[56] References Cited

U.S. PATENT DOCUMENTS

| | | | |
|---|---|---|---|
| 3,946,742 | 3/1976 | Eross | 128/207.17 |
| 4,114,626 | 9/1978 | Beran | 604/180 |
| 4,142,527 | 3/1979 | Garcia | 604/180 |
| 4,249,529 | 2/1981 | Nestor et al. | 128/207.17 |
| 4,270,529 | 6/1981 | Muto | 128/207.17 |
| 4,326,515 | 3/1982 | Shaffer et al. | 128/207.17 |
| 4,516,293 | 5/1985 | Beran | 128/207.17 |
| 4,683,882 | 8/1987 | Laird | 128/207.17 |
| 4,699,616 | 10/1987 | Nowak et al. | 128/DIG. 26 |
| 4,874,380 | 10/1989 | Hesketh | 604/180 |
| 4,906,234 | 3/1990 | Voychehovski | 128/207.17 |
| 4,932,943 | 6/1990 | Novak | 604/180 |
| 4,986,815 | 1/1991 | Schneider | 128/DIG. 26 |
| 5,009,227 | 4/1991 | Niewwstad | 128/207.17 |
| 5,073,170 | 12/1991 | Schneider | 604/180 |
| 5,076,269 | 12/1991 | Austin | 128/207.17 |
| 5,224,935 | 7/1993 | Hollands | 604/180 |

FOREIGN PATENT DOCUMENTS

| | | | |
|---|---|---|---|
| 2643269 | 8/1990 | France | 604/180 |
| 9114472 | 10/1991 | WIPO | 128/207.17 |

OTHER PUBLICATIONS

Model of Disclosed Invention.
Model and Photograph of "Second and New" Device, date undisclosed.

*Primary Examiner*—John G. Weiss
*Assistant Examiner*—K. M. Reichle
*Attorney, Agent, or Firm*—Charles F. Meroni, Jr.

[57] ABSTRACT

A device for holding an endotracheal tube at a corner of a human patient's mouth to allow the mouth to remain free of obstruction in event aspiration of stomach contents occurs. The device includes a relatively stiff clamp holder pad. The clamp holder pad has a clamp holder mounted at one end thereof. A clamp for holding an endotracheal tube at one side of a person's mouth to leave a central area of a person's mouth between its corners free of obstructions to enable regurgitated foods and fluids to flow more freely from a person's mouth is provided. The clamp holder having a releasable fastener securing the clamp to the clamp holder. Straps are attached to the relatively stiff clamp holder pad and are positioned topside thereof on opposite sides of the clamp. The straps have "VELCRO" fasteners for securing the straps when the straps are wrapped around a patient's head extending directly underneath a patient's nose and across a patient's chin to firmly position the device on a patient's head at one side of a patient's mouth.

9 Claims, 2 Drawing Sheets

U.S. Patent    Sep. 3, 1996    Sheet 1 of 2    5,551,421
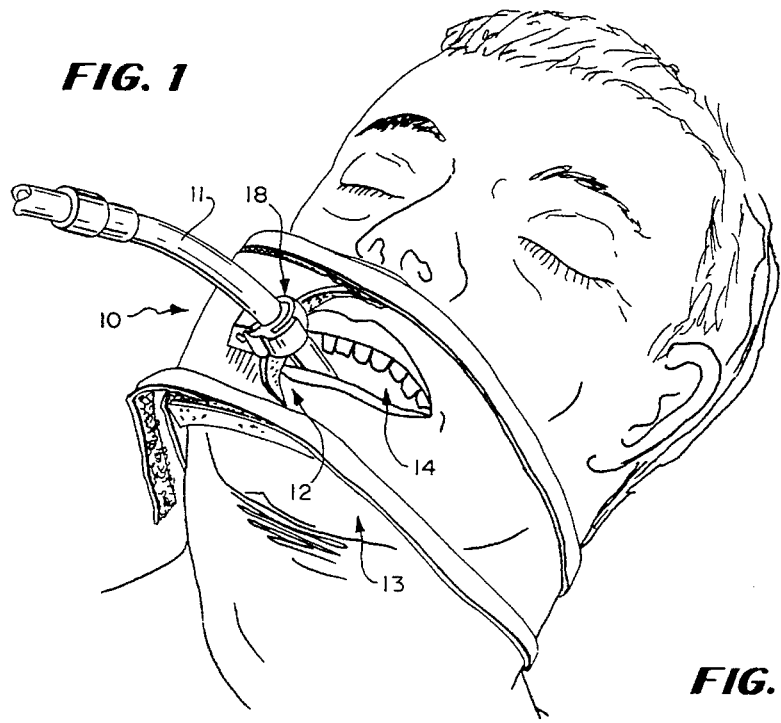
FIG. 1
FIG. 2
FIG. 3
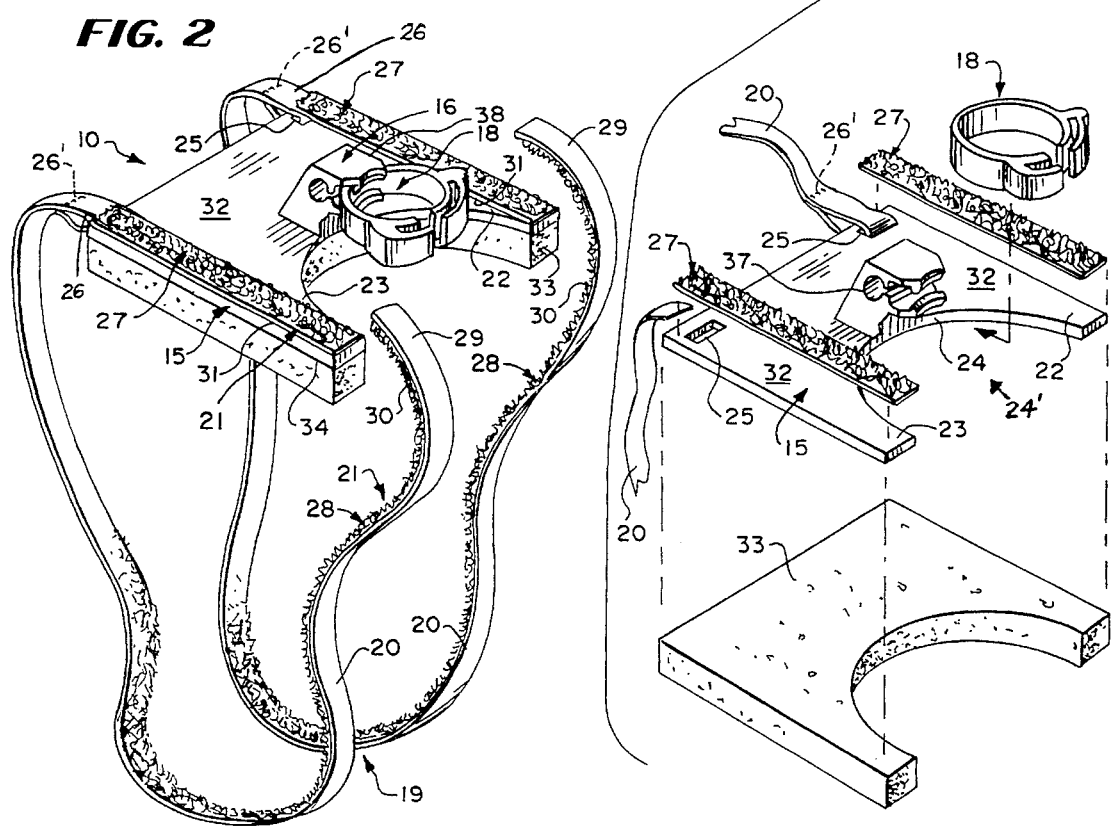

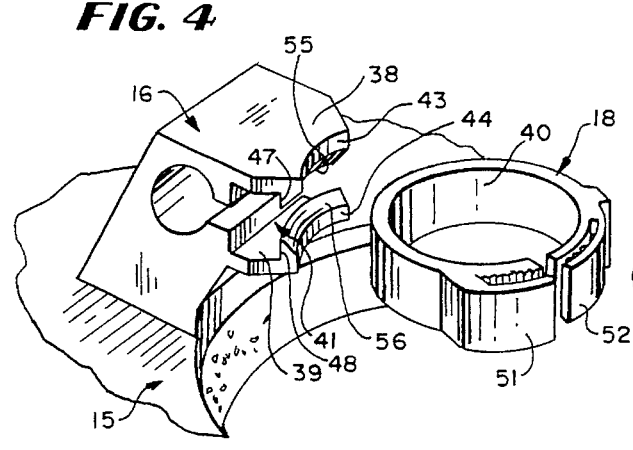
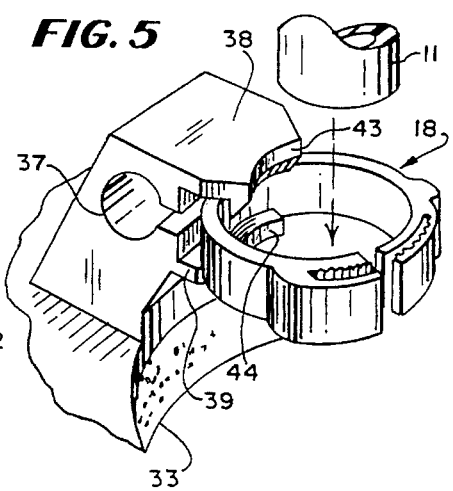
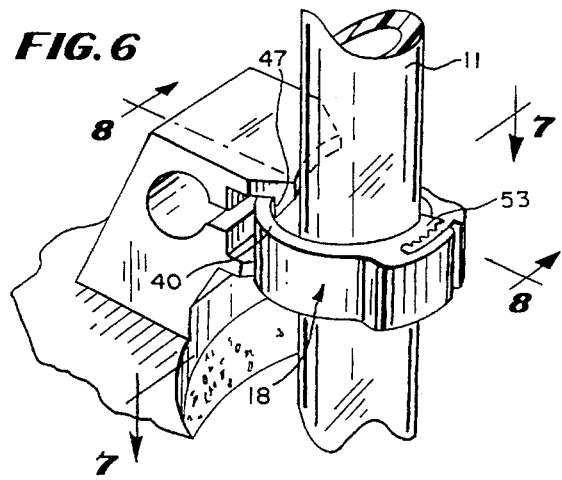
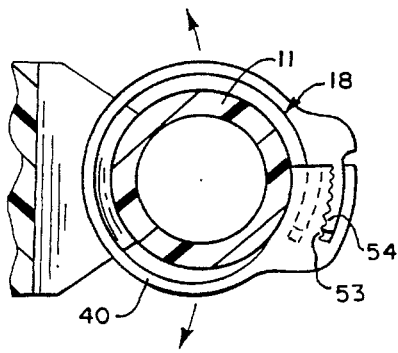
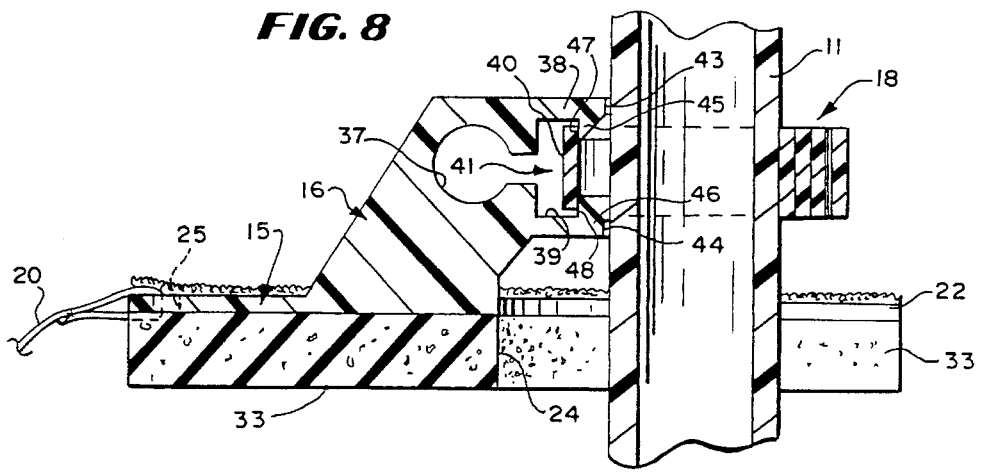

DEVICE FOR SECUREMENT OF AN ENDOTRACHEAL TUBE IN A PATIENT'S MOUTH

This is a continuation of application Ser. No. 07/861,465 filed on Apr. 1,1992, now abandoned.

BACKGROUND OF THE INVENTION

Field of the Invention

This invention relates to a device which holds an endotracheal tube securely at one side of a patient's mouth to provide a temporary air passage between the lungs and atmosphere when the mouth, throat, or trachea are obstructed. The invention is particularly constructed so that it can be affixed so as to be positively located and held at one side of a patient's cheek area, and has a clamp for holding the endotracheal tube at this one side of the person's mouth so that should the person become nauseous and should stomach contents be aspirated, the mucus, foods and fluids vomited will be free to flow from the person's mouth in such a way that the device will cause a minimum amount of impairment in the free flow of the aspirated materials for discharge from the person's mouth.

Heretofore, a number of different devices have been known for securing an endotracheal tube within a patient's tracheal lumen, and these prior art devices have been so constructed and used that the endotracheal tube and tube holding device would be centered on a person's mouth beneath the person's nose rather than being positioned at one side of the mouth. Such prior art devices can be found in a number of different teachings in the prior art, and attention is called to a few of these patents which show a variety of these types of devices, as follows:

| Inventor's Name | Title of Patent | U.S. Pat. No. |
| --- | --- | --- |
| James O. Elam | Esophago-Pharyngeal Airway | 4,090,518 |
| Mark A. Shaffer et al | Endotracheal Tube Retainer | 4,326,515 |
| Anthony V. Beran | Tube Holder | 4,392,857 |
| Carmelo Dali | Nasal Cannula | 4,367,735 |

The intention is believed to be an improvement over those previously above identified patented devices which are here presented to show the general state of the art. More specifically, the invention is concerned with a new and improved device that can be used to secure an endotracheal tube in such a way that the endotracheal tube will be extended through a person's mouth at one side of the mouth so that if regurgitation occurs, the potential danger that the stomach's contents might be aspirated into the lungs can be substantially minimized since the regurgitated contents can flow more freely from a person's mouth where the device for holding the endotracheal tube is located on one side of a person's mouth rather than in the middle or beneath the nose.

SUMMARY OF THE INVENTION

The invention relates to a device for holding an endotracheal tube at a corner of a human patient's mouth to allow the mouth to remain freer of obstruction in event aspiration of stomach contents occurs. The device comprises a relatively stiff clamp holder pad. The clamp holder pad has a clamp holder mounted at one end thereof. A clamp for holding an endotracheal tube at one side of a person's mouth to leave a central area of a person's mouth between its corners freer of obstructions to enable regurgitated foods and fluids to flow more freely from a person's mouth is provided. The clamp holder having releasable means securing the clamp to the clamp holder. Straps are attached to the relatively stiff clamp holder pad and are positioned topside thereof on opposite sides of the clamp. The straps having fasteners for securing the straps when the straps are wrapped around a patient's head extending directly underneath a patient's nose and across a patient's chin to firmly position the device on a patient's head at one side of a patient's mouth.

Other features of the invention relate to the clamp holder pad and the clamp holder being molded of a synthetic plastic as a one piece unit.

Yet other features of the invention relate to the clamp holder pad have a pair of spaced apart pad legs with one of the pad legs being engageable against an upper lip area beneath a person's nose and with another of the pad legs being engageable against a person's chin area beneath the person's mouth.

According to yet further features of the invention, the clamp holder has a pair of superimposed flexible jaws extended over in spaced relation above an arcuate opening in one end of the relatively stiff clamp holder pad, the clamp holder having a keyhole slot located between the jaws enabling the jaws to be flexible relative to one another, said clamp having a band, the jaws having a band slot between them for receiving said band, inclined lead-in jaw surfaces provided on said jaws, the inclined lead-in jaw surfaces being positioned in planes that intersect inwardly of outer ends of said jaws, the band slot being located behind the lead-in surfaces with said band being retainingly engageable and disengageable from said slots by relatively moving said jaws with respect to one another.

Yet other and further features of the invention concern our device having its jaws provided with a band slot located therebetween, the jaws having inclined lead-in surfaces where the lead-in surfaces are positioned in planes that intersect in said band slot inwardly of outer ends of said jaws, and a soft cotton pad secured to an underside of said stiff clamp holder pad for engagement against a person's face.

BRIEF DESCRIPTION OF THE DRAWINGS

FIG. 1 is a diagrammatic view showing the manner of attachment of the invention for holding an endotracheal tube in place at a corner of a human patient's mouth;

FIG. 2 is an enlarged perspective view showing a clamp holder in readiness for assembly with a clamp to be secured with an endotracheal tube;

FIG. 3 is an enlarged fragmentary exploded view of the device shown in FIG. 2;

FIG. 4 is an enlarged fragmentary diagrammatic view illustrating components of the invention with a tube clamp being positioned in readiness for assembly with a clamp holder;

FIG. 5 is an enlarged fragmentary view similar to FIG. 4 only showing the clamp mounted in assembly with the clamp holder and further illustrating the clamp in an open position in readiness to receive the endotracheal tube;

FIG. 6 is an enlarged fragmentary assembly view similar to FIG. 5 only illustrating the endotracheal tube being

3 mounted in assembly with the clamp to clamp the tube to a relatively stiff supporting pad;

FIG. 7 is an enlarged fragmentary cross-sectional view taken on the line 7—7 looking in the direction indicated by the arrow as seen in FIG. 6; and FIG. 8 is an enlarged fragmentary cross-sectional view taken on the line 8—8 looking in the direction indicated by the arrows as seen in FIG. 6.

DESCRIPTION OF THE PREFERRED EMBODIMENT

According to the invention and important features thereof, a device 10 is provided for holding an endotracheal tube 11 at a corner 12 of a person's 13 mouth 14 to allow the mouth and air passageways to remain freer of obstruction should a person's stomach contents be aspirated. In other words, by the placement of the endotracheal tube 11 at the corner of a person's mouth, rather than at a central location in the mouth, any foods that might be aspirated would be freer to flow from the person's mouth where the tube 11 is located at a corner rather than at a middle or central area of the mouth such as it would be located where it would be centered on a person's nose according to known prior art practices.

The invention 10 includes a relatively stiff clamp holder pad 15 to be positioned at the corner of the patient's mouth, and. The clamp holder pad 15 adapted to be in engagement with a patient's check as shown in FIG. 1 has a clamp holder 16 formed integral therewith where the pad 15 and the holder 16 are molded together from a suitable synthetic plastic material as a one piece unit, as illustrated in the drawings (FIGS. 3, 8). The clamp holder pad has the clamp holder cantilever mounted from one end of the pad(FIG. 8) so that an end portion of the clamp holder is projected away from a center portion of the clamp holder pad(FIG. 2). The center portion being defined as the portion of the clamp holder pad approximately midway between the straps. The clamp holder holds a clamp adjacent the corner of the patient's mouth.

Cooperable with the clamp holder 16 is a suitable ring-shaped clamp 18 comprised of a synthetic plastic material which is of a now conventional patented type that is now available in the marketplace. In order to clamp the device 10 to a person's head as shown in FIG. 1, a strap structure 19 is provided that includes a pair of straps 20,20. Opposite ends of each of these straps are attachable in different ways to the relatively stiff clamp holder pad 15. To this end, each strap 20 has a "VELCRO" retainer structure 21. In U.S. Pat. No. 3,658,107, it is stated that "a tape or fabric is manufactured as a fastener and sold under the trade name 'Velcro' by Velcro Corporation of 681 Fifth Avenue, New York, N.Y. 10022." Fasteners of this type hereinafter referred to as "VELCRO" fasteners are found in U.S. Pat. Nos. 3,658,107, 3,732,600, 4,591,148 and 4,708,183. Upper and lower pad extensions or legs 22,23 (FIG. 2) are provided, which pad legs 22,23 are separated by an arcuately curved head portion 24. The clamp holder 16 is located topside midway of the arcuately curved head portion 24 or, in other words, at the center portion. A semi-circular opening 24' is defined by the curved head portion 24 and the legs 22,23. In other words, the pad has an arcuate opening at one end partially defined by a pair of transversely spaced pad legs, 22,23. The pad legs define means for extending partially above and below a person's lips, respectively, when the pad is located at the corner of the person's mouth, to a point directly beneath the person's nose and to a point on the person's chin beneath the person's lips, respectively.

Head slots 25,25 are provided in an opposite upright part edge of the relatively stiff clamp holder pad 15 as seen in FIG. 3. The straps 20,20 have ends 26,26 that extend through the slots 25,25 which ends are sewn at 26',26' to the straps to permanently attach one end of each of the straps to the holder pad 15 and through the slots 25,25.

Opposite strap ends 29,29 of the straps 20,20 carry "VELCRO" attachment portions 28 possessed of hooks 30,30 as exist in a "VELCRO" fastener or retainer structure 21. The "VELCRO" retainer sections 27,27 are glued at 31,31 along bottom surfaces to a top pad or exterior surface 32 of the pad 15.

A soft cotton pad 33 underlies the hard pad 15, and is glued at 34 thereto. The holder 16 has a keyhole-shaped slot 37. The clamp holder has resiliently yieldable upper and lower hook-shaped slot defining jaws or legs 38,39. The upper and lower jaws or legs 38,39 are provided with gripping jaw terminals 45,46 securing or operatively engaging a band 40 of the clamp 18 in a band slot 41 between the jaws 38 and 39. The upper and lower hook-shaped legs 38,39 have outwardly facing upper and lower curved faces 43,44 for engagement to act as curved segments located radially inside the band 40 when the band is secured in assembly with the clamp holder and engageable with spaced curved portions of the tube 11 for assisting in supporting the tube in assembly with the clamp. The upper and lower hook-shaped legs 38,39 form the end portion of the clamp holder.

When the clamp 18 is tightly engaged with the tube 11, the clamp band 40 is engaged against inside jaw shoulders 47,48 (FIG. 8) while the tube is drawn against outside curved jaw faces 43,44 to co-act with the clamp to hold the tube 11 permanently in place when the clamp is tight against these curved surfaces or bases. The ring-shaped clamp 18 is known to one skilled in the art. It has confronting slotted clamp ends 51 and 52 which are arcuately movable towards one another to cause toothed clamp jaws 53,54 (FIG. 7) to be engaged in slots defined in the clamp ends 51 and 52. To release the clamp jaws, the jaws are movable relative to one another in an axial direction to disengage the toothed jaws and release them from the slots provided in the slotted clamp ends 51 and 52 thereby releasing the tube 11.

In order to assemble the components of our device 10 preparatory to attaching the tube 11 thereto, the clamp 18 is engaged with the spreadable jaws 38 and 39 and pushed into engagement with the lead-in surfaces 55 and 56 causing the band to be lodged in the slot 41. Then the tube 11 can be caused to move in the direction indicated by an arrow shown in FIG. 5 into engagement with the clamp when the slotted clamp ends 51 and 52 are in an open position as shown in FIGS. 4 and 5. Then, the slotted clamp ends 51 and 52 are engagable together by moving them circumferentially towards one another causing the toothed clamp jaws to be engaged snugly about the tube 11 thereby drawing the tube 11 in a direction towards and possibly against the curved surfaces 43 and 44 as seen in FIG. 8. At this point in time, the band 40 which is lodged in the slot 41 is engaged against the jaw shoulders 47 and 48.

As discussed before, the clamp holder 16 and the pad 15 are preferably molded together from a suitable synthetic plastic in one piece. This pad and clamp holder 15 and 16 can be manufactured from a material known as "DELRIN" 500 and the like. Which material is manufactured and sold by DuPont Corporation.

Although the invention has been described by reference to some embodiments it is not intended that the novel apparatus be limited thereby, but that modifications thereof are intended to be included as falling within the broad scope and spirit of the foregoing disclosure, the following claims and the appended drawings.

We claim:

1. A device for holding an endotrachcal tube at a corner of a human patient's mouth to allow the mouth to remain free of obstruction in event aspiration of stomach contents occurs comprising a relatively stiff clamp holder pad to be positioned at the corner of the patient's mouth in engagement against a patient's cheek, clamping means for releasably clamping the endotracheal tube at one side of the patient's mouth adjacent the corner to leave a central area of the patient's mouth between its corners free of obstructions to enable regurgitated foods and fluids to flow more freely from the patient's mouth, the clamp holder pad having holding means, cantilever mounted from one end of the pad so that an end portion of the holding means is projected away from a center portion of the clamp holder pad, for holding said clamping means adjacent the corner of the patient's mouth, the holding means having releasable means for releasably securing the clamping means to said holding means, the releasable means including a pair of flexible hook-shaped jaws operatively engageable with the clamping means, straps attached to said relatively stiff clamp holder pad at a position on an exterior surface thereof on opposite sides of said clamping means, said straps having means for securing a strap wrapped around a patient's head and extending directly underneath a patient's nose and another strap wrapped around the patient's head and extending across a patient's chin to firmly position the device on the patient's head at the one side of the patient's mouth.

2. The device of claim 1, wherein the clamp holder pad and the holding means are molded of a synthetic plastic as a one piece unit.

3. The device of claim 1, wherein the clamp holder pad has a pair of spaced apart pad legs with one of said pad legs being engageable against an upper lip area beneath the patient's nose and with the other of said pad legs being engageable against an area of the patient's chin beneath the patient's mouth.

4. The device of claim 1, wherein the jaws have inclined lead-in surfaces where the surfaces are positioned in planes that intersect inwardly of outer ends of said jaws, and the jaws having a band slot therebetween located inwardly behind the lead-in surfaces.

5. The device of claim 1, wherein the jaws are extended over and in spaced relation above an arcuate opening in the relatively stiff clamp holder pad, the releasable means having a keyhole slot located between the jaws enabling the jaws to be flexible relative to one another, the jaws having a band slot between them, said clamping means having a band movable into and out of engagement with said band slot upon flexing of said jaws, the jaws having curved outer surfaces for engagement with the endotracheal tube when the tube is secured in assembly with said clamping means.

6. The device of claim 1, wherein the jaws are extended over and in spaced relation above an arcuate opening in said one end of the relatively stiff clamp holder pad, the holding means having a keyhole slot located between the jaws enabling the jaws to be flexible relative to one another, said clamping means having a band, the jaws having a band slot between them for receiving said band, inclined lead-in jaw surfaces provided on said jaws, the inclined lead-in jaw surfaces being positioned in planes that intersect inwardly of outer ends of said jaws, said band slot being located behind the lead-in surfaces with said band being retainingly engageable and disengageable from said band slot by relatively moving said jaws with respect to one another.

7. The device of claim 1, wherein said clamp holder pad has an arcuately-shaped opening at said one end thereof for receiving the endotracheal tube in said clamping means at one side of the patient's mouth, the jaws projected in overlying relation to the arcuately-shaped opening in said pad, said clamping means having a band, the jaws co-acting to hold said band in assembly with said holding means, the endotracheal tube being extendible through the band and with outer surfaces of the holding means being curved so as to act as curved segments located radially inside of said band when the band is secured in assembly with the holding means, the curved surfaces being engageable with the endotrachcal tube for assisting in supporting the tube in assembly with the clamping means.

8. An endotracheal tube holder device for placement at a corner of a person's mouth to allow the mouth to remain free of obstruction in event aspiration of stomach contents occurs comprising a relatively stiff clamp holder pad for engagement against a person's cheek having an arcuate opening at one end partially defined by a pair of transversely spaced pad legs, the pad legs defining means for extending partially above and below a person's lips, respectively, when the pad is located at the corner of the person's mouth, to a point directly beneath a person's nose and to a point on a person's chin beneath the person's lips, respectively, the clamp holder pad having a clamp holder cantilever mounted from one end of the pad so that an end portion of the clamp holder is projected away from a center portion of the clamp holder pad, means for releasably clamping the endotracheal tube to the clamp holder at one side of the person's mouth to leave a central area of the person's mouth between its corners free of obstructions to enable regurgitated foods and fluids to flow more freely from the person's mouth, the means for releasably clamping the endotracheal tube including the clamp holder having a pair of flexible hook-shaped jaws operatively engaging a clamp releasably connectable to the endotracheal tube, and straps attached to said clamp holder pad legs, respectively, on an exterior surface thereof, said straps having means for securing a strap wrapped around a person's head and extending directly underneath the person's nose and another strap wrapped around the person's head and extending across the person's chin.

9. A device for holding an endotracheal tube at a corner of a human patient's mouth to allow the mouth to remain free of obstruction in event aspiration of stomach contents occurs comprising a relatively stiff clamp holder pad to be positioned at the corner of the patient's mouth, clamping means for releasably clamping the endotracheal tube at one side of the patient's mouth adjacent the corner to leave a central area of the patient's mouth between its corners free of obstructions to enable regurgitated foods and fluids to flow more freely from the patient's mouth, the clamp holder pad having holding means mounted from one end of the pad for holding said clamping means adjacent the corner of the patient's mouth, the holding means having releasable means for releasably securing the clamping means to said holding means, the releasable means includes a pair of flexible hook-shaped jaws, the jaws having inclined lead-in surfaces where the surfaces are positioned in planes that intersect inwardly of outer ends of said jaws, the jaws having a band slot therebetween located inwardly behind the lead-in surfaces, straps attached to said relatively stiff clamp holder pad positioned on an exterior surface thereof on opposite sides of said clamping means, said straps having means for securing a strap wrapped around a patient's head and extending directly underneath a patient's nose and another strap wrapped around the patient's head, and extending across a patient's chin to firmly position the device on the patient's head at the one side of the patient's mouth.

* * * * *